(12) United States Patent
Martinez

(10) Patent No.: US 7,851,647 B2
(45) Date of Patent: Dec. 14, 2010

(54) THREE CARBON PRECURSOR SYNTHONS

(76) Inventor: Rodolfo A. Martinez, 1 Juego Rd., Santa Fe, NM (US) 87508

( * ) Notice: Subject to any disclaimer, the term of this patent is extended or adjusted under 35 U.S.C. 154(b) by 434 days.

(21) Appl. No.: 12/098,098

(22) Filed: Apr. 4, 2008

(65) Prior Publication Data

US 2008/0255384 A1    Oct. 16, 2008

Related U.S. Application Data

(60) Provisional application No. 60/923,107, filed on Apr. 11, 2007, provisional application No. 60/948,359, filed on Jul. 6, 2007.

(51) Int. Cl.
 *C07C 69/52* (2006.01)
 *C07C 57/02* (2006.01)
(52) U.S. Cl. ................. 560/205; 562/598
(58) Field of Classification Search .............. None
 See application file for complete search history.

(56) References Cited

U.S. PATENT DOCUMENTS

| | | |
|---|---|---|
| 4,113,863 A | 9/1978 | Baumgarth et al. |
| 6,312,867 B1 | 11/2001 | Kinsho et al. |
| 2007/0004929 A1* | 1/2007 | Martinez et al. .............. 556/87 |

OTHER PUBLICATIONS

PCT—Notification of Transmittal of the International Search Report and the Written Opinion of the International Searching Authority, or the Declaration, Date of Mailing: Jul. 7, 2008.

* cited by examiner

*Primary Examiner*—Karl J Puttlitz
(74) *Attorney, Agent, or Firm*—Richard H. Krukar; Luis M. Ortiz; Kermit D. Lopez

(57) ABSTRACT

Alkoxy[$^{13}$C]methyl phenyl sulfone is a precursor to the production of Lithium (E)-β-Alkoxy[1,2,3-$^{13}$C$_3$]acrylate and thence Alkoxy (E)-β-Alkoxy[1,2,3-$^{13}$C$_3$]acrylate. Alkoxy (E)-β-Alkoxy[1,2,3-$^{13}$C$_3$]acrylate can then serve as a precursor for the production of a number of other isotopically labeled compounds. Similar chemistry using Alkoxy[$^{14}$C] methyl phenyl sulfone as the precursor can yield $^{14}$C labeled compounds. High purity precursors ensure that the new compounds are also highly pure.

12 Claims, 3 Drawing Sheets

THREE CARBON PRECURSOR SYNTHONS

CROSS REFERENCE TO RELATED APPLICATIONS

This patent application claims the priority and benefit of two U.S. Provisional Patent Applications the first being No. 60/923,107 filed Apr. 11, 2007 entitled "Carbon Labeled, Isotopically Labeled C13 Molecules and also deuterium Labeled Molecules Based on the Chemistry of C13 Methyl Phenyl Sulfide" and the second being No. 60/948,359 filed Jul. 6, 2007 and titled "Synthesis of Isotopically Tagged Synons". Both 60/923,107 and 60/948,359 are herein incorporated by reference.

TECHNICAL FIELD

The present invention relates to labeled compounds and more particularly to compounds derived from isotopically enriched Alkoxy[$^{13}$C]methyl phenyl sulfone or Alkoxy[$^{14}$C] methyl phenyl sulfone. As such, the isotopic tags can be carbon-13 or carbon-14.

BACKGROUND OF THE INVENTION

Phenyl sulfones are extremely useful for the synthesis of many important biochemical's and pharmaceuticals. Additionally, the use of stable isotopes has long been considered to be a promising tool in biomedical diagnosis. Furthermore, the past two decades have seen a tremendous leap forward in the development of very sophisticated instrumentation for the detection of disease and for probing biological structure and function. In conjunction with this a need for very complicated isotopically labeled materials has been on the increase.

Another area of application has become critical after the "9/11" tragedies. The use of stable isotopes in molecules (metabolites) for the rapid detection of threat agents (chemical and biological) is now in large demand. Current isotopic labeling precursors and techniques, however, have made this a very daunting task.

In order to meet the urgent and growing demand, high purity isotopically labeled compounds are needed.

BRIEF SUMMARY

The following summary is provided to facilitate an understanding of some of the innovative features unique to the embodiments and is not intended to be a full description. A full appreciation of the various aspects of the embodiments can be gained by taking the entire specification, claims, drawings, and abstract as a whole.

It is therefore an aspect of the embodiments to use Alkoxy [$^{13}$C]methyl phenyl sulfone to produce Lithium (E)-β-Alkoxy[1,2,3-$^{13}$C$_3$]acrylate and thence Alkoxy (E)-β-Alkoxy[1,2,3-$^{13}$C$_3$]acrylate. Alkoxy (E)-β-Alkoxy[1,2,3-$^{13}$C$_3$]acrylate can then serve as a precursor for the production of a number of other isotopically labeled compounds. Similar chemistry using Alkoxy[$^{14}$C]methyl phenyl sulfone as the precursor can yield $^{14}$C labeled compounds. High purity precursors ensure that the new compounds are also highly pure. For example, Alkoxy[$^{13}$C]methyl phenyl sulfone in concentrations over X percent can be obtained using currently known techniques. As such, the previously unknown compounds herein disclosed are nearly 100 percent pure and are certainly over 80 percent pure.

BRIEF DESCRIPTION OF THE DRAWINGS

The accompanying figures, in which like reference numerals refer to identical or functionally similar elements throughout the separate views and which are incorporated in and form a part of the specification, further illustrate aspects of the embodiments and, together with the background, brief summary, and detailed description serve to explain the principles of the embodiments.

DETAILED DESCRIPTION

Figure 1:
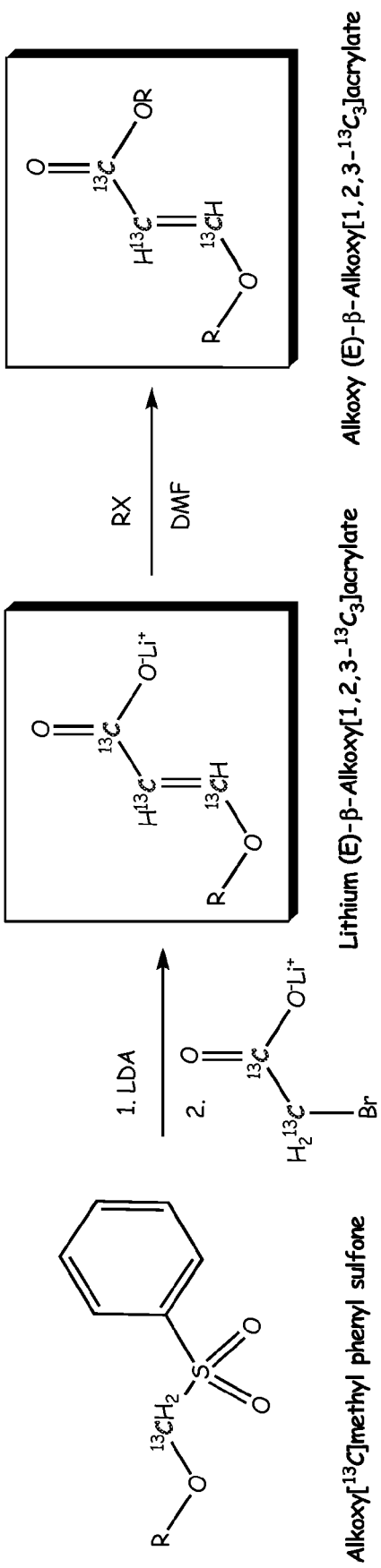
FIG. 1 illustrates using Alkoxy[$^{13}$C]methyl phenyl sulfone to produce Lithium (E)-β-Alkoxy[1,2,3-$^{13}$C$_3$]acrylate and thence Alkoxy (E)-β-Alkoxy[1,2,3-$^{13}$C$_3$]acrylate in accordance with aspects of the embodiments.
Figure 2A:
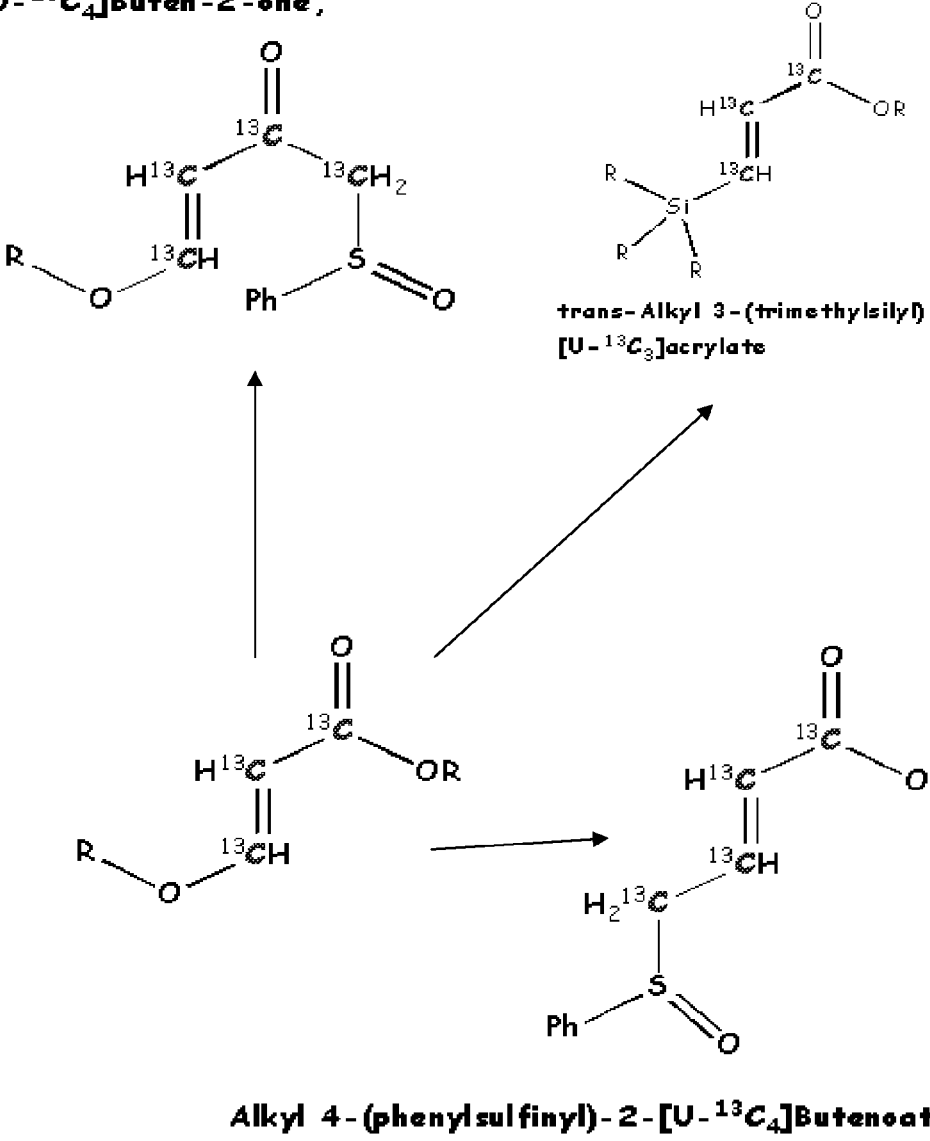
FIG. 2 illustrates reactions of Alkoxy (E)-β-Alkoxy[1,2,3-$^{13}$C$_3$]acrylate in accordance with aspects of the embodiments.
Figure 2B:
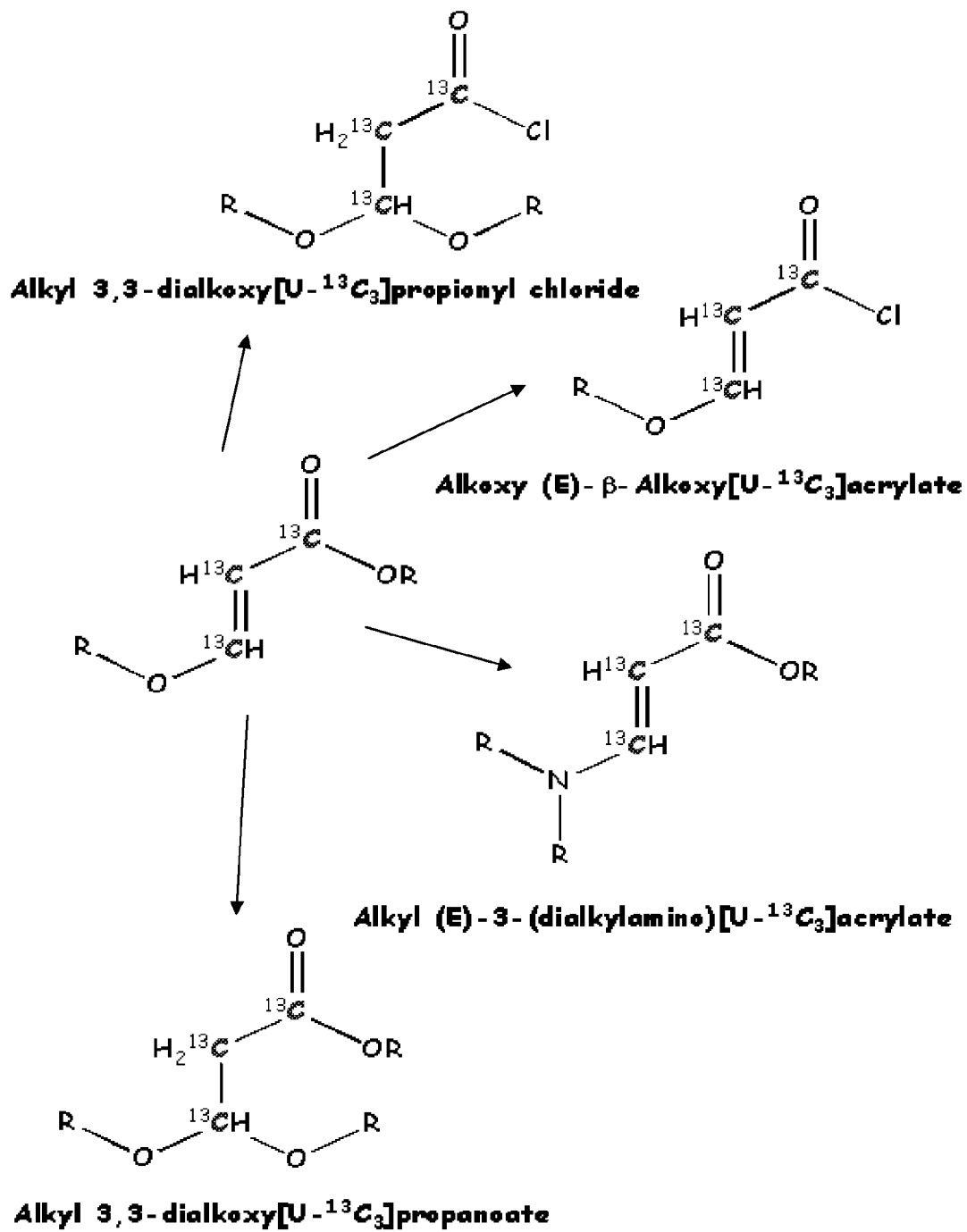

The following description contains a series of examples wherein previously known labeled compounds are processed to yield highly pure labeled compounds that are not previously known.

Synthesis of ethyl-3,3-diethoxy[U-$^{13}$C]propionate

Ethoxy[1$^{13}$C]-methylphenyl sulfone (15.0 g, 0.075 mol) and dry tetrahydrofuran (THF) (150 mL) were placed in a 250 mL round bottom flask equipped with a magnetic stir bar and a rubber septum fitted to nitrogen inlet. The resultant solution was purged under a constant flow of nitrogen after which it was submerged in an ethanol/dry ice bath bringing it to a temperature of −78° C. The solution was then equilibrated at that temperature by allowing it to stir for a period of 15 minutes. Lithium diisopropyl amide (LDA) (109.4 mL, 0.164 mol.) was added slowly via a syringe to the mixture. The reaction mixture was stirred for 45 minutes to ensure complete anion formation. At that point, a solution of [U-$^{13}$C$_2$] bromoacetic acetic acid (11.56 g, 0.0825 mol in THF (15 mL)) was added slowly to the reaction mixture. This mixture was allowed to stir for an additional hour. To this reaction mixture was added another portion of LDA (54.7 mL, 0.0835 mol.). $^{13}$CNMR of an aliquot taken in D$_2$O, showed the quantitative formation of ethoxy[U-$^{13}$C$_3$]acrylate. After stirring for an additional hour, the mixture was partitioned between dichloromethane (125 mL) and deionized water (200 mL). The aqueous layer was separated and poured into a separatory funnel containing dichloromethane (125 mL). This mixture was then acidified with 1N HCl to a pH 2 and the organic layer was separated, dried over anhydrous sodium sulfate, filtered and then concentrated under reduced pressure which afforded 13.25 g of a crude mixture of trans-ethoxy[U-$^{13}$C$_3$]-propenoic acid and benzene sulfinic acid. This crude mixture was immediately dissolved in absolute ethanol (200 mL) and after about 5 mins of stirring, amberlyst (9.0 g) was added. The entire mixture was then heated to reflux for 4 hrs. After this period, $^{13}$CNMR of an aliquot taken in CDCl$_3$ showed the complete formation of the desired product. The heating was discontinued and the flask was allowed to cool to room temperature. The residual amberlyst was filtered off using a frit funnel packed with celite then, the celite cake was rinsed with dichloromethane (2×25 mL). The resultant solution was poured into a separatory funnel containing hexane (150 mL) and deionized water (300 mL). The hexane layer was separated, filtered into a round bottom flask and concentrated using a rotary evaporator set at 25° C., 75 torr, which gave 15.78 g as a mixture of ethyl phenylsulfinate and the titled compound as pale yellow oil. The entire crude was chromatographed by DCC to afford 8.89 g, 61.35% of the title compound as a pale yellow liquid which was used in subsequent reactions without further purification. The spectra data are as follows:

$^1$HNMR (300 MHz in CDCl$_3$ with 0.03% TMS)/δ: 5.249, 5.244, 5.228, 5.225, 5.209, 5.205, 4.701, 4.698, 4.678, 4.661 (dtd, $^{13}$CH J 164.36, 6.98, 1.46); δ: 4.197, 4.186, 4.173, 4.163 4.149, 4.138, 4.126, 4.115 (qd 2H J 7.36, 3.31 Hz); δ: 4.162-3.49 (two unresolved qd which appears as a multiplet 4H); δ: 2.903, 2.881, 2.861, 2.839, 2.469, 2.448, 2.426, 2.406 (ddd $^{13}$CH$_2$, J 130.16, 12.87, 6.62 Hz); δ: 1.288, 1.265, 1.241, 1.224, 1.200, 1.177 (two sets of triplets 9H J 6.97 Hz). $^{13}$CNMR (75 MHz in CDCl$_3$) δ: 170.583, 169.802, (d $^{13}$COOEt, J 58.86 Hz), δ: 100.149, 99.543 (d $^{13}$CH J 45.77 Hz); δ: 40.850, 40.229, 40.070, 39.464 (dd $^{13}$CH$_2$ 58.86, 45.77 Hz).

Synthesis of 3,3-diethoxy[U-$^{13}$C]propionic acid

A 50/50 mixture of ethyl-3,3-diethoxy[U-$^{13}$C]propionate and benzene sulfinic acid ethyl ester (8.89 g) was treated with 1N NaOH (70 mL) in a 250 mL round bottom flask. The mixture was stirred at room temperature for an hour, after which it was poured into a separatory funnel containing dichloromethane (50 mL). This mixture was then acidified and extracted with dichloromethane at pH values of 6, 4, 2 and 1. The organic layers extracted at pH values of 4 and 6, were combined, dried over anhydrous sodium sulfate, filtered and then concentrated in vacuo to afford 3.1 g, (81.36%) of the titled compound as pale yellow oil. Comments: This reaction was used as a purification technique for ethyl 3,3-diethoxy [U-$^{13}$C]propionate.

The spectra data are as follows: 1HNMR (300 MHz in CDCl$_3$ with 0.03% TMS)/δ: 10.67 (s 1H), δ: 5.24, 5.22, 5.20, 4.69, 4.67, 4.66 (dtd J 165.82, 5.88, 1.47 1H), δ: 3.78-3.51 (unresolved multiplet), δ: 2.96, 2.94, 2.92, 2.90, 2.53, 2.51, 2.48, 2.47 (ddd J 129.79, 12.87, 5.88 2H), δ: 1.23, 1.21, 1.18 (t J 7.35 Hz) $^{13}$CNMR (75 MHz in CDCl$_3$) δ: 175.79, 175.04 (d J 56.68) δ: 99.51, 98.90 (d J 45.78), δ: 62.00, δ: 40.30, 39.69, 39.56, 38.94 (dd J 56.68, 45.79) δ: 15.10, 15.05 (d J 3.27).

Esterification of 3,3-diethoxy-[U-$^{13}$C]propionic acid to ethyl-3,3-diethoxy[U-$^{13}$C]propionate A sample of 3,3-Diethoxy[U-$^{13}$C]propionic acid (1.5 g, 9.0 mmol), amberlsyt (3.5 g) and absolute ethanol (15 mL) were placed in a 100 mL round bottom flask equipped with a reflux condenser and a magnetic stir bar. This mixture was heated to reflux with constant stirring for 4 hours. $^{13}$CNMR of an aliquot taken in CDCl$_3$ indicated the complete formation of the desired product. The heating was discontinued and the flask was allowed to cool to room temperature. The residual amberlyst was filtered off using a frit funnel packed with celite and then the celite cake was rinsed with dichloromethane. The resultant solution was poured into a separatory funnel containing hexane (35 mL) and DI water (40 mL). The hexane layer was separated, dried over anhydrous sodium sulfate, filtered and then concentrated using a rotary evaporator set at 25° C., 75 torr which gave 1.52 g, 87.34% of the titled compound as yellow liquid. The crude obtained from this reaction was used in subsequent reactions without further purification. The spectra data are as follows:

$^1$HNMR (300 MHz in CDCl$_3$ with 0.03% TMS)/δ: 5.25, 5.24, 5.23, 5.22, 5.21, 5.20, 4.70, 4.69, 4.67, 4.66 (dtd, $^{13}$CH J 164.36, 6.98, 1.46); δ: 4.19, 4.18, 4.17, 4.16 4.14, 4.14, 4.13, 4.12 (qd 2H J 7.36, 3.31). δ: 4.16-3.49 (two unresolved qd which appears as a multiplet 4H); δ: 2.90, 2.88, 2.86, 2.84, 2.47, 2.45, 2.43, 2.41 (ddd $^{13}$CH$_2$, J 130.16, 12.87, 6.62); δ: 1.29, 1.27, 1.24, 1.22, 1.20, 1.18 (two sets of triplets 9H J 6.97). $^{13}$CNMR (75 MHz in CDCl$_3$) δ: 170.58, 169.80, (d $^{13}$COOEt, J 58.86 Hz), δ: 100.15, 99.54 (d $^{13}$CH J 45.77 Hz), δ: 40.85, 40.23, 40.07, 39.46 (dd $^{13}$CH$_2$ 58.86, 45.77 Hz).

Synthesis of 3-ethoxy[U-$^{13}$C]-acrylic acid

Diethoxy[U-$^{13}$C]propionic acid (80 wt %, 1.17 g, 0.0057 mol) and dry tetrahydrofuran (10 mL) were placed in an oven dried 100 mL round bottom flask equipped with a magnetic stir bar and a rubber septum fitted to a nitrogen inlet. This mixture was then subjected to a constant flow of nitrogen and equilibrated at a temperature of –12° C. by submerging in an ethanol/ice bath. After about 10 minutes, a THF solution of lithium diisopropyl amide (10.5 mL, 15.75 mmol) was added. $^{13}$CNMR analysis of an aliquot taken in D$_2$O showed the complete formation of the desired product. The reaction mixture was then transferred into a 250 mL separatory funnel containing dichloromethane (30 mL) and DI water (10 mL). This mixture was then acidified with 1N HCl to a pH of 2 and the organic layer was separated, dried over anhydrous sodium sulfate, filtered and concentrated in vacuo to afford 0.58 g, 75% of [1, 2, 3, $^{13}$C$_3$]-3-ethoxy acrylic acid.

The NMR data are as follows; 1HNMR (300 MHz in CDCl$_3$ with 0.03% TMS) δ: 10.42 (s OH), δ: 8.02, 8.00, 7.99, 7.98, 7.97, 7.96, 7.95, 7.93, 7.92, 7.40, 7.39, 7.38, 7.37, 7.36, 7.35, 7.34, (dddd J 183.1, 12.13, 6.25, 3.31, 1H), δ: 5.47, 5.46, 5.43, 5.42, 4.93, 4.91, 4.88, 4.87, (ddd J 163.25, 12.5, 3.68 1H), δ: 3.99, 3.98, 3.96, 3.95, 3.94, 3.93, 3.92, 3.91 (qd J 2.58, 6.99 2H), δ: 1.38, 1.35, 1.33 (t J 6.98 3H). $^{13}$CNMR (75 MHz in CDCl$_3$ with 0.03% TMS) δ: 174.30, 174.24, 174.28, 173.21 (dd J 77.39, 77.38), δ: 165.00, 164.922, 163.96, 163.89 (dd J 78.47, 77.38), δ: 96.64, 95.60, 94.57 (dd J 78.47, 77.38) δ: 67.69, 67.25, 67.06, 66.48 (dd J 47.96, 57.77) and δ: 14.34.

Synthesis of 4,4 diethoxy-1-(phenylsulfinyl) [1-$^{13}$C]butan-2-one

[1-$^{13}$C]-Methyl phenyl sulfoxide (3.0 g, 0.021 mol) and anhydrous tetrahydrofuran (20 mL) were placed in a 250 mL oven dried round bottom flask equipped with a magnetic stir bar and a rubber septum fitted to a nitrogen inlet. This mixture was subjected under a constant flow of nitrogen after which it was equilibrated at −78° C. for 10 minutes in an ethanol (absolute)/dry ice bath. Lithium diisopropylamide (18.4 mL, 0.027 mol 1.3 eq) was added slowly to the mixture. After about 45 minutes of stirring, ethyl-3,3-diethoxy propionate (90 wt %, 4.25 g, 4.38 mL, and 0.022 mols) was added neat to the reaction mixture. Initial NMR showed the formation of an intense peak at 69 ppm, indicative of the product and some starting material at 44 ppm (a ratio of 85% to 15% product starting material respectively). The entire mixture was allowed to stir for a period of 4.0 hours after which it was partitioned between dichloromethane (75 mL) and deionized water (30 mL). The aqueous layer was separated and transferred into a separatory funnel containing dichloromethane (50 mL). This mixture was acidified to a pH of 2, and then the organic layer was separated and thoroughly washed with DI water (2×100 mL). The combine organic layers were dried over anhydrous sodium sulfate then filtered and concentrated using a rotary evaporator to afford 5.1 g, 85.3% of the titled compound as red liquid that was used without further purification.

The NMR data are as follows: $^1$HNMR δ: 7.68-7.52 (5H, m), δ: 4.843, 4.824, 4.87 (1H, t J 5.51), δ: 4.226, 4.178, 4.154, 3.75 (1H, dd J 140.83, 14.36), δ: 4.216, 4.167, 4.106, 3.71 (1 H dd J 140.82, 14.71) δ: 3.689, 3.680, 3.662, 3.655, 3.648, 3.639, 3.632, 3.625, 3.615, 3.607, 3.601, 3.584, 3.578, 3.552, 3.534, 3.529, 3.522, 3.511, 3.506, 3.498, 3.487, 3.480, 3.474, 3.64, 3.457. (4H, two quartets that appear as a multiplet), δ: 2.856, 2.824, 2.793, 2.774, 2.724, (2H ddd J 15.07, 9.92, 4.05), δ: 1.199, 1.182, 1.176, 1.158, 1.154, 1.135 (6H, t J 5.70). $^{13}$CNMR (75 MHz in CDCl$_3$) δ: 199.30, 198.78 (d J 41.41 C=O), 143.16, 131.56, 129.44, 124.12 (aromatic carbons) δ: 99.355 (CH) δ: 69.439 ($^{13}$CH$_2$), δ: 62.49, 62.47 (—OCH$_2$) 49.25, 49.09 (—CH$_2$) 15.18.

Synthesis of 4,4 diethoxy-1-(phenyl sulfinyl)[U-$^{13}$C$_4$]butan-2-one

The same procedure as above in experiment 15 was repeated using [$^{13}$C]-methylphenyl sulfoxide (0.93 g, 6.5 mmol), ethyl 3,3-diethoxy[U$^{13}$C$_3$]propionate (1.4 g, 7.3 mmol) and LDA (6.5 mL, 9.75 mmol). This reaction afforded 1.59 g, 85% of the titled compound as a yellow fluid. This crude product was used in the next reaction without further purification.

The NMR data are as follows, $^1$HNMR δ: 7.68-7.51 (m 5H), δ: 5.11-4.52 (dtd J 163.62, 5.51, 1.84 1H), δ: 4.23-3.75 (ddd J 140.46 13.98 4.42, 1H), δ: 3.74-3.42 (unresolved multiplets), δ: 3.08-2.50 (dddd J 128.32, 15.07, 9.19, 5.14, 2H), δ: 1.19-1.13 (t 3H) $^{13}$CNMR (75 MHz in CDCl$_3$) δ: 199.19, 198.96, 198.41, (dd J 40.33, 41.41 $^{13}$C=O), δ: 143.10, 131.51, 129.39, 124.09 (aromatic carbons); δ: 99.63, 99.02 (d 45.78, $^{13}$CH), δ: 69.43, 69.27, 68.91, 68.75 (dd, J 39.24, 39.24, PhSO$^{13}$CH$_3$); 62.46 (OCH$_2$); δ: 49.79, 49.63, 49.24, 49.19, 49.08, 49.04, 48.48, (ddd 45.78, 41.42, 11.99 $^{13}$CH$_2$); δ: 15.15, 15.10 (d 3.27 CH$_3$).

Synthesis of 4,4-diethoxy-2-[1-$^{13}$C]butanone

A solution of 4,4-diethoxy-1-(phenylsulfinyl)[1-$^{13}$C]butan-2-one (0.5 g 1.75 mmol) and ethanol (5 mL absolute) was stirred at room temperature under a constant flow of nitrogen and a scoop of wet Raney nickel 2800 was added. The reaction mixture immediately changed from a yellow to an orange color. TLC analysis (80% EtOAc/20% Hexane) at that point showed the presence of some starting material. After about 30 minutes of reaction time, another scoop of Raney nickel was added. The reaction mixture changed from an orange to milky appearance and TLC analysis showed the complete disappearance of starting material. The Raney nickel was filtered using a frit funnel packed with celite and the celite cake was rinsed continuously with ethanol (caution: dry Raney nickel is pyrophoric, so always keep it wet). The filtrate was partitioned between dichloromethane (20 mL) and DI water (10 mL) and the organic layer was separated, dried over anhydrous sodium sulfate, filtered into a round bottom and then concentrated under reduced pressure to afford 0.25 g, 89.2% of a pale yellow fluid. (Rf=0.48, 80% Hex/20% EtOAc).

The NMR data are as follows: $^1$HNMR (300 MHz in CDCl$_3$ with 0.03% TMS) δ: 4.92, 4.90, 4.88 (t J 5.53 1H), δ: 3.69, 3.68, 3.67, 3.66, 3.65, 3.64, 3.61, 3.58, 3.56, 3.55, 3.53, 3.51, 3.50, (m pseudo chirality effect, 4H), δ: 2.76, 2.74 (d J 5.88 2H), δ: 2.39, 1.97 (d, J 127.21 $^{13}$CH$_3$), δ: 1.22, 1.19, 1.17 (t, J 6.98, 3H). $^{13}$CNMR (75 MHz in CDCl$_3$) δ: 205.96, 205.43 (d J 40.33 C=O), δ: 99.73, (CH(OR)$_2$) δ: 62.14, δ: 48.30, 48.13 (d J 13.08 CH$_2$) 31.06 (s $^{13}$CH$_3$), and 15.12.

Synthesis of 4,4-diethoxy[U-$^{13}$C$_4$]butan-2-one

The procedure above in experiment 17 was repeated with 4,4-diethoxy-1-(phenylsulfinyl)[U-$^{13}$C]butan-2-one (210 mg, 0.729 mmol) as starring material. This experiment afforded 0.107 g, 90.23% of the title compound as a pale yellow fluid. This crude was used in subsequent reactions without further purification.

The NMR data are as follows: 1HNMR (300 MHz in CDCl$_3$ with 0.03% TMS) δ: 5.19, 5.18, 5.17, 5.16, 5.15, 5.14, 4.65, 4.64, 4.63, 4.62, 4.61, 4.60, (dtd J 162.88, 5.52, 1.47 Hz, $^{13}$CH), δ: 3.72-3.47 (m, pseudo chirality effect, 4H), δ: 2.98, 2.96, 2.94, 2.93, 2.56, 2.54, 2.52, 2.50 (ddd, J 127.58, 11.58, 5.88 Hz, $^{13}$CH$_2$), δ: 2.41, 2.40, 2.39, 2.38, 1.983, 1.97, 1.963, 1.960 (ddd, J 127.28, 6.28, 1.47 Hz $^{13}$CH$_3$); δ: 1.22, 1.19, 1.17 (t J 6.98 3H). $^{13}$CNMR (75 MHz in CDCl$_3$) δ: 206.25, 205.72, 205.18 (t J 40.33, $^{13}$C=O), 100.02, 99.41 (d 45.77 $^{13}$CH), δ: 62.37, 62.13, 61.87 (dd, 17.44, 19.62 OCH$_2$), δ: 48.85, 48.67, 48.33, 48.25, 44.15, 44.07, 47.72, 47.53 (ddd J 45.77, 40.34, 12.72 $^{13}$CH$_2$), δ: 31.41, 31.23, 30.85, 30.68 (dd J 41.41, 41.42 $^{13}$CH$_3$), δ: 15.14, 15.10 (d J 3.27 CH$_3$).

Synthesis of 4,4-diethoxy-1-(phenylsulfinyl)[1-$^{13}$C]-butan-2-ol

A sample of 4,4-diethoxy-1-(phenylsulfinyl) [1-$^{13}$C]butan-2-one (0.54 g, 1.89 mmol) and anhydrous THF (5 mL) were mixed in 100 mL round bottom flask equipped with a magnetic stir bar. After about 5 mins of stirring, sodium borohydride (0.07 g, 1.89 mmol) was added as solid to the mixture at room temperature. The reaction was allowed to stir for 3 hours and $^{13}$CNMR at that point showed the complete formation of the desired diastereotopic peaks. The reaction mixture was quenched in saturated ammonium chloride after which it was then poured into a 250 mL separatory funnel containing dichloromethane (25 mL) and DI water (10 mL). The organic layer was separated, dried over anhydrous sodium sulfate, filtered and then concentrated using a rotary evaporator to afford 0.43 g, 80% of the titled compound as yellow oil.

Synthesis of 1-(phenylsulfinyl) [1-$^{13}$C]pent-3-en-2one

[1-$^{13}$C]-Methylphenyl sulfoxide (1 g 7.09 mmol) and dry THF were placed in an oven dried 100 mL round bottom flask equipped with a magnetic stir bar and a rubber septum fitted to a nitrogen inlet. The mixture was flushed under a constant flow of nitrogen and set to −78° C. using dry ice and ethanol (100%) bath. Lithium diisopropylamide (5.2 mL, of 1.5 M in THF) was added slowly for a period of 5.0 minutes and after about 45 minutes of stirring, trans-ethyl crotonate (0.6 mL, 7.8 mmol) was added slowly to the reaction mixture. $^{13}$CNMR of an aliquot in CDCl$_3$ at that point indicated the formation of the product at 65 ppm and some starting material (a ratio of 85%:15% for product and starting material respectively). The reaction mixture was then poured in to a 250 mL separatory funnel containing dichloromethane (30 mL) and DI water (15 mL). The aqueous layer was extracted and poured into another 250 mL separatory funnel containing 20 mL of dichloromethane. This mixture was acidified to a pH of 2 and the organic layer was separated, dried over anhydrous sodium sulfate, filtered and then concentrated in vacuo to afford 1.1 g, 74.3% of a yellow oily liquid (about 10% starting material).

Synthesis of trans-4-(phenylsulfinyl) [4-$^{13}$C]crotonic acid methyl ester

[1-$^{13}$C]-Methyl phenyl sulfoxide (2.5 g, 0.014 mol) and anhydrous THF (20 mL) were mixed in a 100 mL round bottom equipped with a magnetic stir bar and a rubber septum fitted to a nitrogen inlet. This mixture was stirred under a constant flow of nitrogen for a period of 10 minutes, after which it was then equilibrated at −78° C. in an ethanol dry ice bath. After about 10 minutes of equilibration, lithium diisopropylamide (17.7 mL, 1.8 eq) was added slowly for a period of 2 minutes. The resultant mixture was stirred for a period of 45 minutes to ensure complete anion formation. At that point, 3-methoxy acrylic acid methyl ester (2.09 mL, 0.015 mol) was added neat to the reaction mixture still at −78° C. Initial $^{13}$CNMR in CDCl$_3$ showed the formation of a new peak at 59 ppm and some starting material at 44 ppm (a ratio of 80% to 20% product starting material). The reaction mixture was allowed to go for an addition 3.0 hours and $^{13}$CNMR analysis of an aliquot in CDCl$_3$ at that point showed 85% conversion of starting material to product. After about 30 minutes of stirring, the reaction mixture was poured into a separatory funnel containing dichloromethane (75 mL) and deionized water (30 mL). This mixture was acidified to a pH of 2 and the organic layer was extracted (2×50 mL). The combined organic layers were dried over anhydrous sodium sulfate, filtered, and then concentrated using a rotary evaporator to afford 4.2 g of a red fluid. This crude product was purified by dry column chromatography (using 80% EtoAc/20% hexane as the eluent) to afford 2.74 g, 86.9% of the titled compound light red oil, which immediately solidified on standing.

The NMR data are as follows: $^1$HNMR δ: 7.58-7.52 (m 5H); δ: 6.73-6.65 (m unresolved multiplet 1H); δ: 5.93-5.86 (ddd J 15.44, 6.98, 6.25, 1.1); δ: 3.99-3.31 (two sets of ddd J 149.28, 12.87, 7.72, 2H); δ: 3.72 (s 3H). $^{13}$CNMR (75 MHz in CDCl$_3$) δ: 138.60, 131.66, 129.43, 128.48, 59.04 and 55.13 (the carbonyl peak was not seen).

Synthesis of trans-4-ethoxy-1-(phenylsulfinyl)-3-[1-$^{13}$C]buten-2-one

A mixture of 4,4 diethoxy-1-(phenyl sulfinyl)[1-$^{13}$C]-butan-2-one (110 mg, 0.385 mmol), sodium acetate (0.031 g catalytic amount) and toluene (2 mL) was heated under reflux and stirring for 14 hrs. $^{13}$CNMR analysis after this period confirmed 80% conversion of starting material to product. The reaction was allowed to go for additional 4 hours. And after this period, there was no noticeable change in the extent of the reaction. The heating was discontinued and the mixture was allowed to reach room temperature. After cooling to room temperature, the entire mixture was partitioned between dichloromethane (10 mL) and DI water (10 mL). The organic layer was separated, dried over anhydrous sodium sulfate, filtered and concentrated under reduced pressure to afford 100 mg of crude product. The crude product was chromatographed (using silica, and 100% ethyl acetate) to afford 56 mg 62% of pure product. Comment: The low yield in this reaction is due to silica hydrolysis of the enol ether formed, probably to an aldehyde.

The NMR data are as follows: $^1$HNMR (300 MHz in CDCl$_3$ with 0.03% TMS) δ: 7.689, 7.679, 7.6750, 7.665, 7.657, 7.534, 7.5241, 7.528, 7.518, 7.510 (5H, m), δ: 7.599, 7.557 (1H, d J 12.50 typical of trans). δ: 5.667, 5.662, 5.625, 5.621 (1H dd J 12.51, 1.48); δ: 4.22, 4.176, 3.754, 3.709 ($^{13}$C H dd J 140.08, 13.23) δ: 4.04, 3.99, 3.57, 3.532 (13CH dd J 140.08, 13.23). δ: 3.992, 3.968, 3.943, 3.920 (OCH$_2$ q J 7.35); δ: 1.368, 1.343, 1.320 (CH$_3$ t J 6.99).

Synthesis of trans-4-methoxy-1-(phenylsulfinyl)-3-[1-$^{13}$C]buten-2-one

The procedure from the previous experiment was repeated (but for purification) with 4,4-dimethoxy-1-(phenylsulfinyl)[1-$^{13}$C]butan-2-one (1.01 g, 4 mmol) and 0.2 molar equivalence of sodium acetate. This experiment afforded 0.83 g, 97.6% of the title compound as a pale yellow fluid. This crude was used in subsequent reactions without further purification.

The spectra data are as follows:

$^1$HNMR (300 MHz in CDCl$_3$ with 0.03% TMS) δ: 7.67-7.51 (m 6H), δ: 5.66, 5.65, 5.62, 5.61, (dd, J 12.5, 1.47 1H), δ: 4.21, 4.17, 4.04, 4.00 (dd, J 139.4, 13.24, 1H), δ: 3.77, 3.75, 3.58, (dd J 139.4, 13.24 1H), δ: 3.72 (s 3H). $^{13}$CNMR data δ: 189.48, 188.93 (d J 41.2 C=O), δ: 165.32, 143.18, 131.43, 129.27, and 124.12, δ: 106.07, 105.86 (d J 15.26 Hz), 67.5, 58.88

What is claimed is:

1. A labeled compound having the structure:

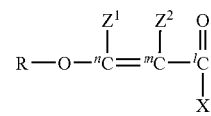

wherein l=12 or 13, m=12 or 13 and n=12 or 13 with the proviso that l, m, and n do not simultaneously equal 12;

wherein R is selected from the group consisting of alkyls and aryls;

wherein $Z^1$ is selected from the group consisting of H and $^2$H;

wherein $Z^2$ is selected from the group consisting of H and $^2$H; and wherein —X is selected from the group consisting of

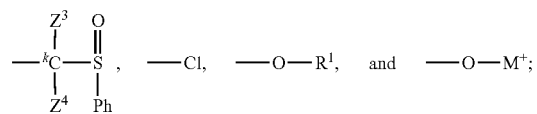

wherein $R^1$ is selected from the group consisting of alkyls and aryls;

wherein k=12 or 13;

wherein $Z^3$ is selected from the group consisting of H and $^2$H;

wherein $Z^4$ is selected from the group consisting of H and $^2$H; and wherein $M^+$ is selected from the group consisting of Li$^+$, Na$^+$, K$^+$.

2. The labeled compound of claim 1 wherein l=13, m=13, n=13, $Z^1$ is H, $Z^2$ is H, and —X is —O—Li$^+$.

3. The labeled compound of claim 1 wherein l=13, m=13, n=13, $Z^1$ is H, $Z^2$ is H, and —X is —O—R$^1$.

4. The labeled compound of claim 1 wherein —X is

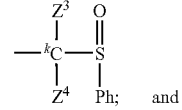

wherein l=13, m=13, n=13, $Z^1$ is H, $Z^2$ is H, $Z^3$ is H, and $Z^4$ is H.

5. The labeled compound of claim 1 wherein l=13, m=13, n=13, $Z^1$ is H, $Z^2$ is H, and —X is —Cl.

6. A labeled compound having the structure:

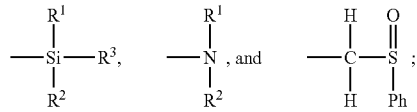

wherein l=12 or 13, m=12 or 13 and n=12 or 13 with the proviso that l, m, and n do not simultaneously equal 12;

wherein $Z^1$ is selected from the group consisting of H and $^2$H;

wherein $Z^2$ is selected from the group consisting of H and $^2$H;

wherein R is selected from the group consisting of alkyls and aryls; and wherein —X is selected from the group consisting of

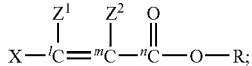

wherein $R^1$ is selected from the group consisting of alkyls and aryls;

wherein $R^2$ is selected from the group consisting of alkyls and aryls; and wherein $R^3$ is selected from the group consisting of alkyls and aryls.

7. The labeled compound of claim 6 wherein X is

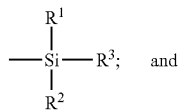

wherein l=13, m=13, n=13, $Z^1$ is H, and $Z^2$ is H.

8. The labeled compound of claim 6 wherein X is

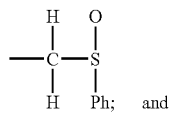

wherein l=13, m=13, n=13, $Z^1$ is H, and $Z^2$ is H.

9. The labeled compound of claim 6 wherein X is

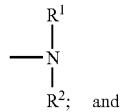

wherein l=13, m=13, n=13, $Z^1$ is H, and $Z^2$ is H.

10. A labeled compound having the structure:

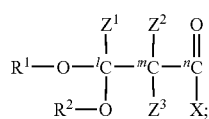

wherein l=12 or 13, m=12 or 13 and n=12 or 13 with the proviso that l, m, and n do not simultaneously equal 12;

wherein $R^1$ is selected from the group consisting of alkyls and aryls;

wherein $R^2$ is selected from the group consisting of alkyls and aryls; and wherein $Z^1$ is selected from the group consisting of H and $^2$H;

wherein $Z^2$ is selected from the group consisting of H and $^2$H;

wherein $Z^3$ is selected from the group consisting of H and $^2$H; and wherein —X is selected from the group consisting of —Cl and —O—R wherein R is selected from the group consisting of alkyls and aryls.

11. The labeled compound of claim 10 wherein l=13, m=13, n=13, $Z^1$ is H, $Z^2$ is H, $Z^3$ is H, and —X is —Cl.

12. The labeled compound of claim 10 wherein l=13, m=13, n=13, $Z^1$ is H, $Z^2$ is H, $Z^3$ is H, and —X is —O—R wherein R is selected from the group consisting of alkyls and aryls.

* * * * *